(12) United States Patent
Mills et al.

(10) Patent No.: US 6,303,384 B1
(45) Date of Patent: Oct. 16, 2001

(54) REAGENT AND METHOD FOR DETECTING AN ADULTERANT IN AN AQUEOUS SAMPLE

(75) Inventors: Susan P. Mills, Ambler, PA (US); John A. Novinski, Leesburg, FL (US); Michael I. Schaffer, Woodland Hills, CA (US)

(73) Assignee: Quest Diagnostics Investments, Inc., San Juan Capistrano, CA (US)

( * ) Notice: Subject to any disclaimer, the term of this patent is extended or adjusted under 35 U.S.C. 154(b) by 0 days.

(21) Appl. No.: 09/517,891

(22) Filed: Mar. 3, 2000

Related U.S. Application Data

(60) Provisional application No. 60/123,299, filed on Mar. 4, 1999.

(51) Int. Cl.[7] .................................................. G01N 33/48
(52) U.S. Cl. ............................ 436/111; 436/110; 436/56; 436/92
(58) Field of Search ................................. 435/37; 436/92, 436/100–125

(56) References Cited

U.S. PATENT DOCUMENTS

| | | | |
|---|---|---|---|
| 3,619,187 | * 11/1971 | Cerwonka | 430/288.1 |
| 3,634,198 | * 1/1972 | Truhan | 435/37 |
| 3,719,491 | * 3/1973 | Mizianty | 430/150 |
| 3,817,705 | 6/1974 | Stein et al. . | |
| 3,961,884 | * 6/1976 | Hertel et al. | 8/21 C |
| 4,058,399 | * 11/1977 | McNeil et al. | 430/259 |
| 4,059,407 | * 11/1977 | Hochstrasser | 422/56 |
| 4,171,222 | * 10/1979 | Frommeld | 430/259 |
| 4,434,235 | 2/1984 | Rabi et al. . | |
| 4,631,255 | * 12/1986 | Takino et al. | 435/37 |
| 4,812,413 | * 3/1989 | Glattstein et al. | 436/92 |
| 4,978,612 | * 12/1990 | Kobayashi et al. | 435/10 |
| 5,032,138 | * 7/1991 | Wolfram et al. | 8/412 |
| 5,464,775 | 11/1995 | Smith et al. . | |
| 5,527,509 | * 6/1996 | Gibson et al. | 422/56 |
| 5,703,266 | * 12/1997 | Lagrange et al. | 558/408 |
| 5,759,860 | 6/1998 | Smith et al. . | |
| 5,801,060 | 9/1998 | Smith . | |
| 5,955,370 | 9/1999 | Kell . | |

FOREIGN PATENT DOCUMENTS

| | | |
|---|---|---|
| 1282653 | 3/1970 | (GB) . |
| 338141 | * 4/1970 | (SU) . |

OTHER PUBLICATIONS

Butler, "The Diazotization of Heterocyclic Primary Amines", Chem. Rev., 1975, v. 75, pp. 241–257.*

* cited by examiner

Primary Examiner—Jill Warden
Assistant Examiner—Yelena Gakh
(74) Attorney, Agent, or Firm—Stout, Uxa, Buyan & Mullins, LLP; Donald E. Stout

(57) ABSTRACT

This invention relates to a reagent and use of that reagent for detecting adulterants in aqueous samples, particularly in biological specimens such as urine samples using a diazo dye precursor such as N,N diethyl-1,4-phenylene diamine and a reagent such as creatinine to stabilize a colored intermediate formed by the reaction of the diamine with nitrite ions for a period sufficient to allow that color to be recorded and compared with a separate peak formed by a halogen-based oxidizing agent which may be present in solution.

10 Claims, 6 Drawing Sheets

REAGENT AND METHOD FOR DETECTING AN ADULTERANT IN AN AQUEOUS SAMPLE

This application claims benefit of Prov. No. 60/123,299 filed Mar. 4, 1999.

AREA OF THE INVENTION

This invention relates to a reagent and use of that reagent for detecting adulterants in aqueous samples, particularly in biological specimens such as urine samples.

BACKGROUND OF THE INVENTION

Adulteration of urine specimens has become an increasingly significant issue in urine drug testing. Products to mask the presence of drugs in the testing process are readily available and new products continue to emerge to stay in the forefront of technology. This invention provides a reagent that can be used in initial testing to screen for the presence of multiple adulterants. The ability of the reagent to detect multiple adulterants is significant because of the limited number of available reagent channels on the instruments used for analysis. This invention provides a reagent and method for detecting in a single, stable, test the presence or absence of three common adulterants: nitrites, pyridinium chlorochromate and hypochlorites like common bleach.

SUMMARY OF THE INVENTION

In a first aspect this invention relates to a colorometric method using a diazo dye precursor for distinguishing between the presence of a nitrite ion and a chlorine-containing oxidizing agent in an aqueous solution, which method comprises adding to an aqueous solution a diazo dye precursor and an agent which stabilizes the colored intermediate formed by the reaction of the nitrite ion with the diazo dye precursor, reading and recording the absorbance of the solution at the peak corresponding to said intermediate formed by the nitrite/diazo dye precursor reaction and the peak corresponding to the color generated by the reaction of the chlorine-containing oxidizing agent and the diazo dye precursor, and subtracting the absorbance of the peak corresponding to the chlorine adulterant from the absorbance of the peak corresponding to the intermediate formed by the nitrite/diazo dye precursor reaction, the readings being taken from a single container or optionally from two different containers.

In a second aspect, this invention relates to an improved colorometric assay for detecting and distinguishing simultaneously in a single pot containing an aqueous solution the presence of a nitrite ion and a halogen-containing oxidizing agent using a diazo dye precursor wherein the improvement comprises using between about 0.1 and 10% weight/volume of a nucleophilic compound as the stabilizing agent for stabilizing the colored intermediate formed by the reaction of the diazo dye precursor and the nitrite ion wherein the stabilized the intermediate is stabilized for at least about 1 minute or more.

In a third aspect this invention relates to a reagent for detecting simultaneously in an aqueous sample the presence of nitrites and chlorine-containing oxidizing agents wherein the reagent comprises a diazo dye precursor and a nucleophile stabilizing agent.

DETAILED DESCRIPTION OF THE INVENTION

Figure 1:
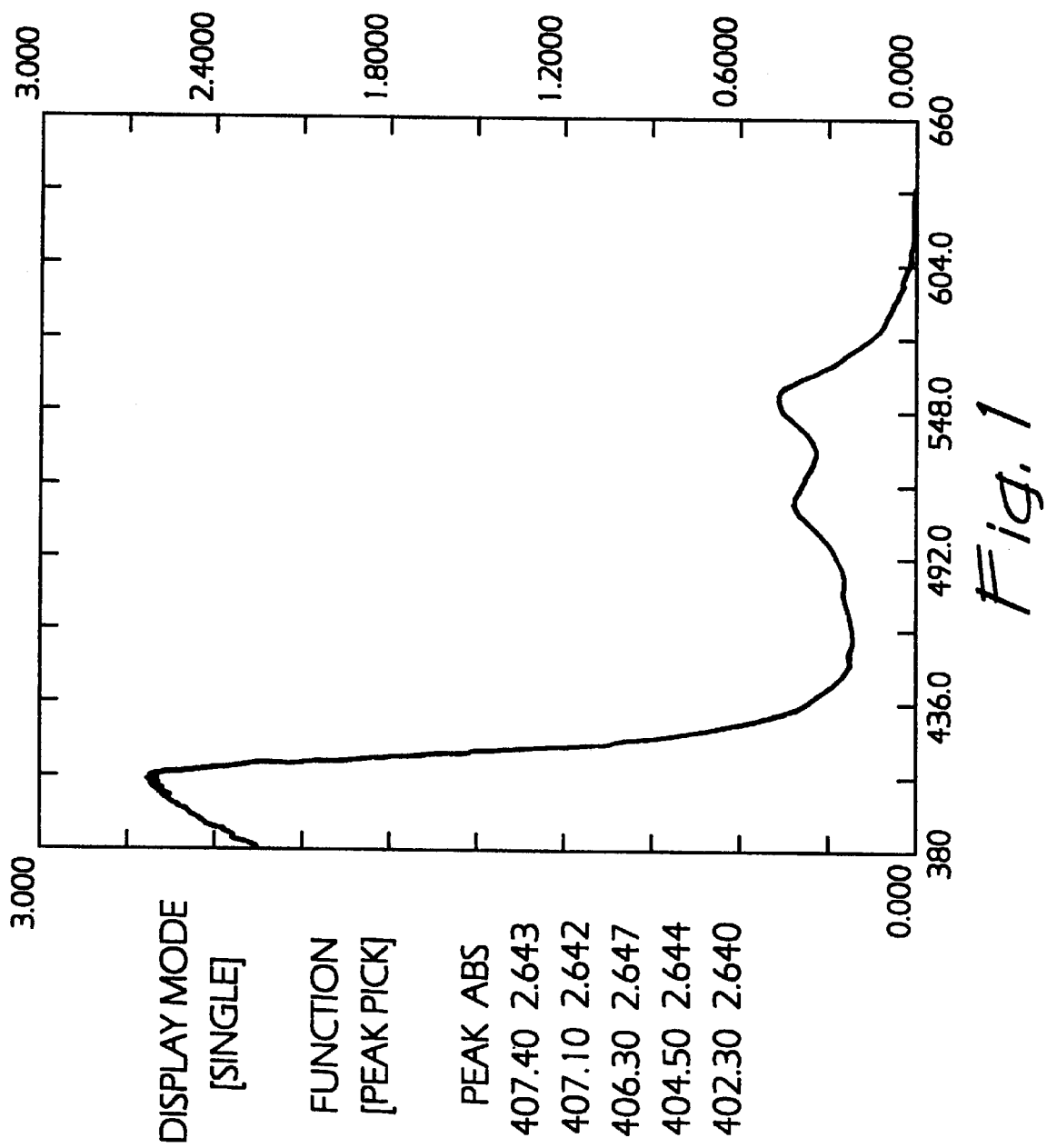
FIG. 1 is a tracing of the visible absorption spectra of a sample treated with DPD and stabilizing agent to which sodium nitrite has been added.

This invention can be used in any situation requiring the identification of the presence of nitrites and halogen-containing oxidizing agents, particularly chlorine-containing oxidizing agents, in the same sample. It has particular applicability in identifying these two chemicals in aqueous samples where drug testing is involved; these two chemicals are added to samples to mask the presence of certain drugs or are added in hopes that they will interfere with the assays used to detect certain drugs. Drug testing is mandated or strongly support by many political and regulatory groups and private industry. Hiring or continued employment may depend on a drug-free test. Urine-based testing is a widely practiced way of detecting the use of controlled substances or substances of abuse. Not too surprisingly those who have found themselves placed in the predicament of having been exposed to certain drugs either purposefully or inadvertently and receiving a request for drug testing have identified and begun using chemicals which mask or interfere with the chemistries used to detect certain drugs. These are called adulterants. Most are chemicals which can be readily obtained by consumers, being that they have a number of uses and are readily available through many consumer or retail channels. Adulterants now showing up with increasing frequency are nitrite salts and certain oxidizing agents, particularly certain chlorochromate salts and the alkali metal hypochlorites, e.g., sodium hypochlorite or common bleach.

This invention provides a way to distinguish between the nitrites and oxidizing agents such as bleaches and chlorochromates in a one-step one-pot test. One aspect of the uniqueness of this assay is that it reads the absorbance of a stabilized intermediate formed by the nitrite ion and the diazo dye precursor rather than reading the absorbance of the diazo dye which forms as a result of reacting with the nitrite. In fact the diazo dye does not give a useful visible absorption spectrum. As a result of stabilizing the colored intermediate formed when the diazo dye precursor reacts with the nitrite ion and the oxidizing agent, two distinct absorbance peaks are obtained, one corresponding to the nitrite/diazo dye precursor intermediate and a second distinct peak corresponding to the oxidization product of the diazo dye precursor. And both can be recorded from the same sample at the same time. Thus the presence or absence of each distinct chemical can be determined and a concentration for each, if present, can be calculated for the same sample with just one pass.

The adulterants that this assay can usefully detect and distinguish between are nitrite salts and halogen-based oxidizing agents, particularly chlorine-containing bleaches such as the chlorochromate salts and the alkali metal salts of hypochlorus acid. The alkali metal salts of nitrite, particularly sodium nitrite, represent the most commonly encountered nitrite adulterants. Pyridinium chlorochromate is the most commonly encountered chlorochromate adulterant. Common household bleach, sodium hypochlorite, is the most frequently encountered hypochlorite drug sample adulterant. Other halogen-based oxidizing agents can also be detected and distinguished using this invention.

A diazo dye precursor combined with a compound which is believed to stabilize the cherry-red colored intermediate formed by the reaction of the diazo dye precursor and the nitrite ion provides the basis for distinguishing between nitrite ions and halogen-based oxidizing agent.

In the context of this invention diazo dye precursors are thought to undergo a coupling reaction with nitrite ions to form a short-lived colored intermediate which then decays to a stable final product which has a different visible absorption spectra from that of the intermediate (Butler, R. M., *Chem Rev*, vol 75, p241 1975; Butler, R. M., *JOC Perkins Trans*, p1357, 1973).

In the course of attempting to develop an assay to identify the presence of abnormal amounts of nitrites and/or oxidizing agents, it was observed that when the diazo dye precursor N,N-diethylphenylene diamine (DPD) was added to urine samples a cherry-red hue formed but faded in a matter of a few seconds followed by the development of a purple color, commonly referred to as a diazo tar. The latter color is useless for analytical purposes. It was thought that the fleeting cherry-red hue may have a visible absorption spectra which might be distinct from that of the visible absorption spectra observed in a urine sample containing a halogen-based oxidizing agent to which the dye precursor had been added. But because the cherry-red color was so fleeting it could not be used to generate reliable reproducible data. However it was noted that in a couple of urine samples spiked with nitrite salts the cherry-red hue appeared to be a bit more persistent. On further investigation it was found that these samples shared a common phenomenon, each had a high creatinine level. Follow-up studies confirmed that adding creatinine stabilized the cherry-red color formed by adding the diazo dye to a nitrite-containing urine sample to a degree that allowed one to reliably and reproducible record the visible absorption spectra of that solution. This data showed that the stabilized DPD/nitrite color had an intense absorption peak at 411 nm and a weak absorption at 540 nm. This is important because samples with halogen-containing oxidizing agents to which DPD were added generated an intense absorption at around 540 nm.

Diazo dye precursors which can be used in this invention are the aromatic diamines such as the phenyl and naphthalene diamines which form diazo compounds under appropriate conditions and in the presence of certain chemicals. Generally speaking the precursors which are useful in this invention are the anilines, the anilinonaphthalenes and the likes of p-arsenilic acid which, when exposed to nitrite ions and halogen-based oxidizing agents, form intermediates exhibit a visible absorption spectra. While the para-substituted diamines usually exhibit the most intense color, ortho-substituted or meta-substituted diamines should work also. It is preferred that one of the nitrogens on the aromatic ring be mono or dialkylated, the other be substituted solely by hydrogen, so that only one of the nitrogens reacts with the nitrite ion and so that only diazo dyes are formed ultimately rather than polmerized imines. The following non-exhaustive list of compounds is believed to be illustrative of diazo dye precursors which can be used in this invention: N,N-diethylphenylene diamine (DPD); 3-(4,5-dimethylthiazolyl-2)-2,5-diphenyl tetrazolium bromide, dimidium bromide; 2,4-dinitro-1,8-naphthalenediol; 2,4-dinitro-1-naphthol; 2,2-diphenyl-1-picrylhydrazyl; N-ethyl-N-(2-hydroxy-3-sulfopropyl)aniline; ethidium bromide; ethyl red; fast blue B, BB and RR and their salts; fast green dyes; fast red dyes; fast violet dyes; fast yellow dyes; cresol red; cresol blue; HABA; 1-(2-hydroxyphenylazo)-2-hydroxyazobenzene; 3-methyl-N-ethyl-N-beta-hydroxyethylaniline; methylene blue, green or violet; methyl green, orange, or red; mordant dyes; naphthol blue or green; n-(1-naphthyl)ethylenediamine hydrochloride; naphthly red; 1-(p-nitrophenylazo)-2-naphthol; pararosaniline; phenol red; p-phenylazoaniline; o-phenylenediamine; 1-(2-pyridylazo)-2-naphthol; pyrocatechol violet; Sudan I, II, III or IV; 2-(2-thiazolyazo)-5-diemthylaminophenol; 1-(2-thiazolylazo)-2-naphthol; and 4-(2-thiazolylazo)resorcinol. DPD is most perferred.

The amount of diamine, or precursor, used will be some concentration which is sufficient to give a useful visible absorption spectra. Generally this will be some amount between about 0.7 and 0.9 mg per mL. Precursor is dissolved in a suitable solvent prior to being added to the test sample. Various solvents can be used so long as the compound dissolves in it. For example when DPD is used it is convenient to first dissolve it in a short-chain organic acid such as formic acid or acetic acid before diluting it further with water.

The stabilizing agent used herein will be a compound that, when combined with a diazo dye, which in the presence of a nitrite ions in solution forms a colored intermediate, stabilizes that colored intermediate formed between the diazo dye and the nitrite ions react, to give a visible absorption spectra which persists for at least about 1 minute. This stabilizing agent is also called herein a nucleophilic compound. It is believed useful stabilizers will have a common characteristic, that of having a pair of electrons to interact with and stabilize the transition state of the observed colored intermediate through which the diazo dye/nitrite reaction proceeds. This is a theoretical explanation of what has been observed; the invention is not to be limited by the theory of how the intermediate might be stabilized. Having discovered that creatinine stabilizes this colored intermediate it is believed other amines can also be used as stabilizing agents. Diethyl amine has been tested and gives equivocal results with DPD but may be efficacious when combined with other diazo dye precursors. Citric acid could used as well.

Time-wise, the color of the intermediate in a target sample should persist for several minutes. While it is recognized that some spectrophotometers can record rapid spectral events, in the context of routine chemical analyses time from sample preparation to spectral processing requires that the sample demonstrate the spectral event for a couple of minutes. And the event must be reliably reproducible so that data from at one time point can be compared against data at another time point. When the purplish color was first observed in nitrite-spiked urine samples to which DPD had been added, the color was so fleeting that in was of no practical value to testing for adulterants. When it was discovered that nucleophiles could stabilize the transition state of the DPD/nitrite reaction, the target became that of creating a test in which the color would persist for at least a minute. That was achieved by identifying creatinine as a stabilizing agent and by manipulating the concentration of creatinine in the reaction pot. Time-wise, the color should persist for at least a minute. Preferably it will persist for at least 2 minutes. To achieve at least about 1 minute of persistence in the color of the intermediate, about 0.1 and 10% by weight/volume of the nucleophile should be present in the test sample.

A preferred embodiment of this invention is one where the dye is N,N-dimethylphenylene diamine (DPD) and creatinine as the stabilizing nucleophile. DPD is available commercially. It is can be purchased from Sigma-Aldrich or ICN Biochemicals.

When a nitrite salt is present the nitrite ion reacts with DPD to produce an intermediate which has an intense absorption peak at 411 nm and a weak absorption peak at 540 nm. If a chlorochromate or hypochlorite ions are present the reaction with DPD produces an intense absorption peak at 540 nm. These two distinct absorption maxima provide a means for distinguishing between nitrites and oxidizing agents. As a practical matter, the cherry-red color of the nitrite/DPD intermediate is measured at 410 nm. In fact the measurement of the cherry-red color can be varied around the 411 nm maximum up to ±5 nm without loss of sensitivity or accuracy. Similarly the 540 nm maximum peak can be read at ±5 nm without loss of sensitivity or accuracy as well. Having identified the existence of a second measurable maximum at 411 nm, the precise choice wavelength in that area of the visible spectrum and that surrounding the 540 nm maximum of the oxidization product is within the skill of the practitioner.

The following examples are provide to illustrate the invention but are not intended to limit it in any fashion or to any degree.

EXAMPLE 1

DPD/Creatinine Reagent

A reagent for detecting the presence of nitrites, chlorochromates or hypochlorites is prepared as follows:

Creatinine (2 gm) is dissolved in 200 mL deionized water and a quantity of deionized water sufficient to make a volume of 500 mL. Then 0.4 gm of N,N diethyl-1,4-phenylene diamine is dissolved in 30 mL of glacial acetic acid. To this solution is then added enough of the creatinine solution prepared above to give a volume of 500 mL. This solution is then ready for use in the colorometric assay for detecting nitrite and chlorine-containing adulterants.

EXAMPLE 2

Figure 2:
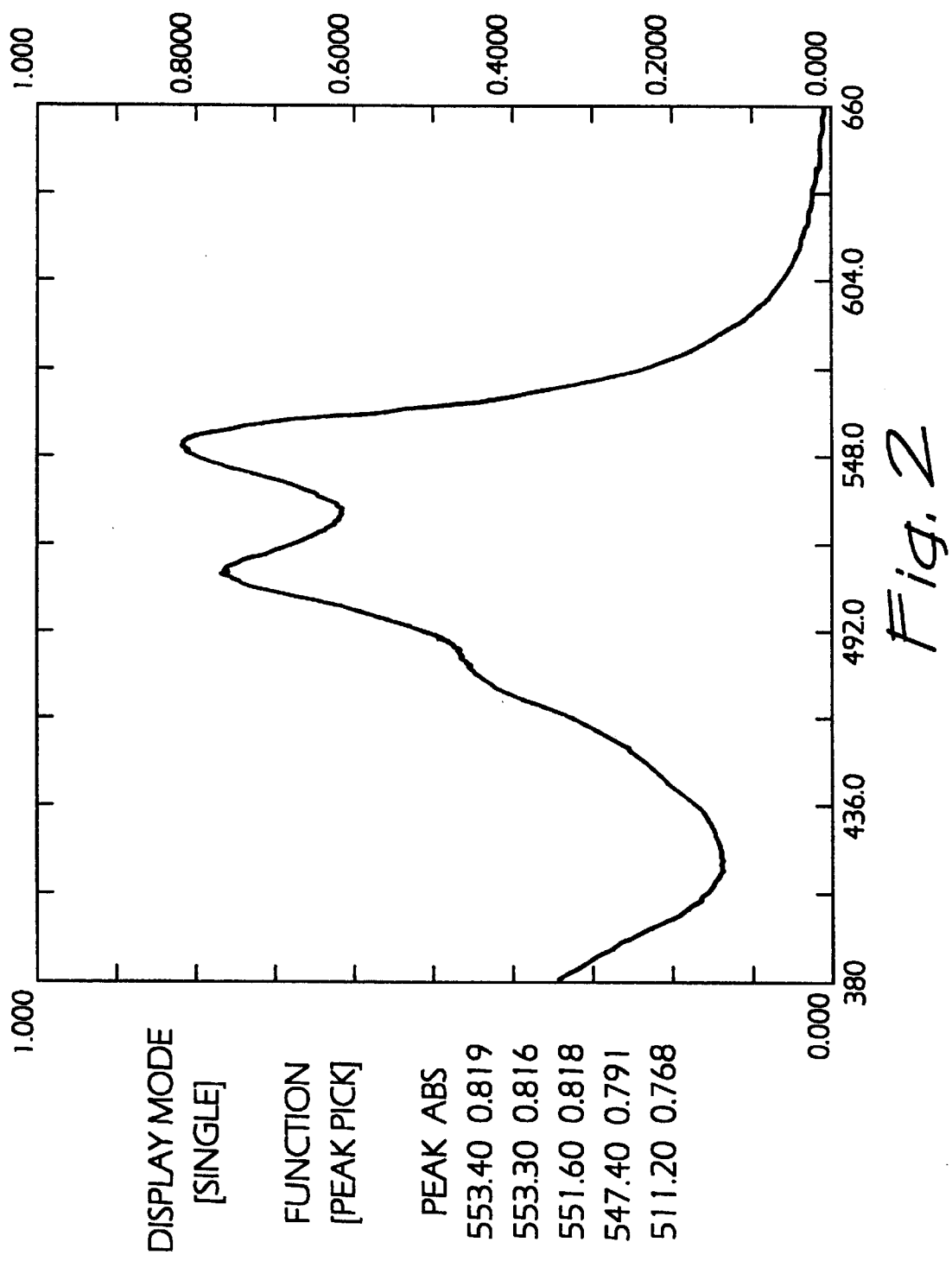
FIG. 2 is a tracing of the visible absorption spectra from a sample containing DPD and stabilizing agent to which sodium hypochlorite has been added.
Figure 3:
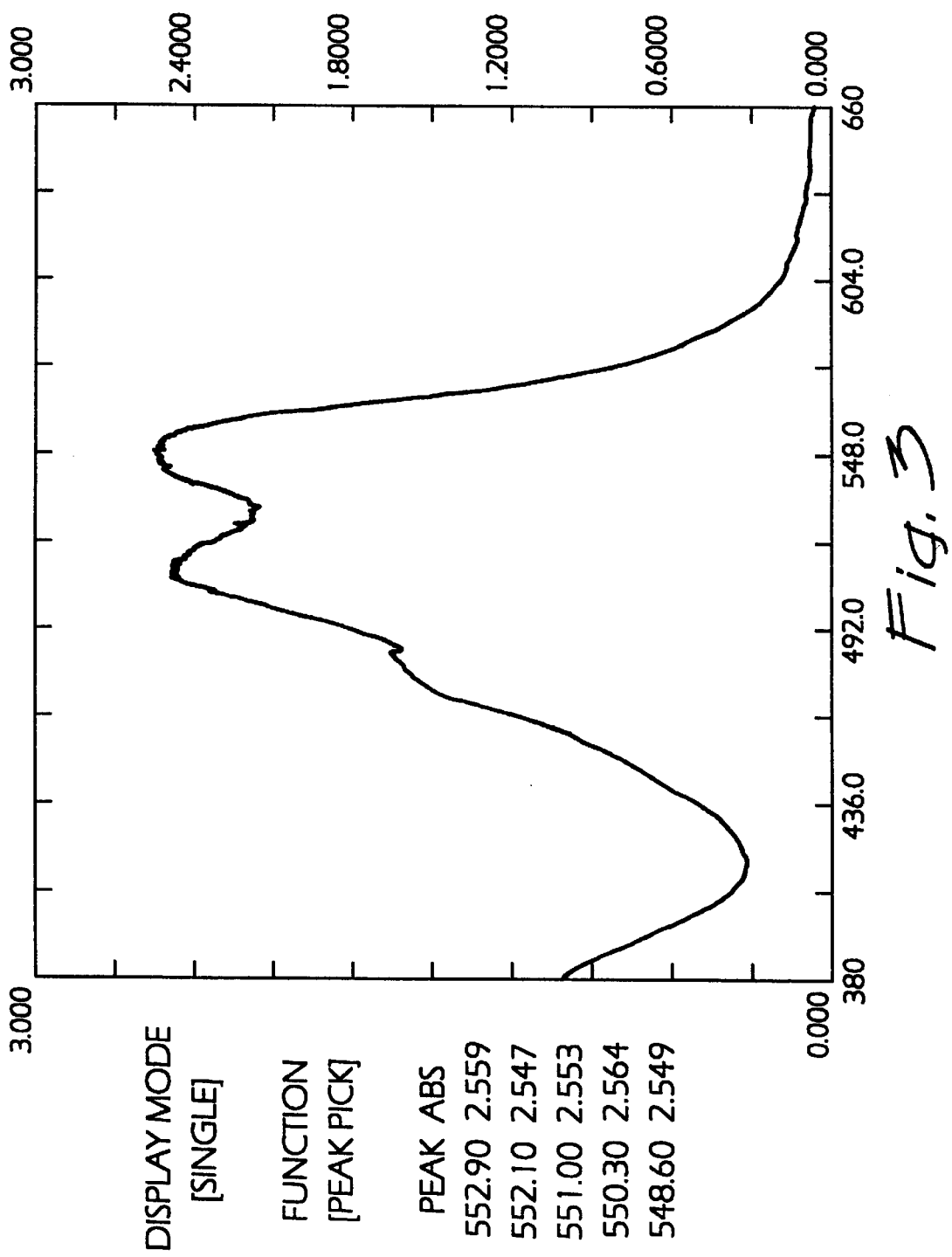
FIG. 3 is a tracing of a visible absorption spectra from a sample containing DPD and stabilizing agent to which pyridinium chlorochromate has been added.

FIGS. 1 and 2 set out the visible spectra for the DPD reagent prepared in Example 1 when sodium nitrite, sodium hypochlorite and pyridinium chlorochromate are added. The visible spectra of the dye that forms with sodium hypochlorite is identical to the visible spectra of the dye that forms from the reaction with pyridinium chlorochromate. It can easily be seen that the sodium nitrite produces a dye with intense absorption at about 411 nm and a weak absorption at around 540 nm. Sodium hypochlorite generates an intense absorption only at 540 nm as does pyridinium chlorochromate. A useful analytical method results which gives positive absorbance for sodium nitrite and negative absorbance for sodium hypochlorite and pyridinium chlorochromate. The method is useful for concentrations of sodium nitrite above two thousand PPM. High concentrations of sodium hypochlorite (20% solutions) increases the lifetime of the cherry-red dye. Results are shown in Table I. These results are based on readings taken with the spectrophotometer set to record at 410 nm and 540 nm.

TABLE 1

Absorbances for NaNO$_2$, NaOCl, and Pyridinium Chlorochromate

| NaNo$_2$ Conc. | Concentration Units | Pyridinium Chloromate | Absorb. | NaOCl | Absorb. |
|---|---|---|---|---|---|
| 200 μg/ml | 122.6 | 125 ppm | −79.25 | 1% | −742.2 |
| 400 μg/ml | 321.1 | 250 ppm | −159.6 | 4% | −1724.8 |
| 500 μg/ml | 338.0 | 500 ppm | −320.2 | 6% | −2212.4 |
| 1000 μg/ml | 534.2 | 1000 ppm | −601.4 | 10% | flagged as high |
| 2000 μg/ml | 972.2 | | | 30% | flagged as high |

TABLE 2

Spectrophotometer Parameters -- Olympus AU8000

| Samepl Vol. | 3 μl | Wavelength 1 | 410 nm | measuring pt | cycle 2 |
|---|---|---|---|---|---|
| Reagent Vol. | 250 μl | Wavelength 2 | 540 nm | | |
| Dilution Vol. | 250 μl | method endpoint | | | |

EXAMPLE 2

Validation Studies

Validation studies were performed to evaluate the following parameters for nitrite, pyridinium chlorochromate and sodium hypochlorite:

Linearity—the linear range at multiple concentration ranges above and below the cutoff were evaluated.

Precision—Intra-run precision was evaluated at the concentration ranges used for linearity evaluation. Inter-run precision was evaluated on quality control samples spiked at +25% and −25% of cutoff.

Correlation—Nitrite: Specimens were tested for nitrite using a current nitrite reagent and DPD and creatinine as prepared in Example 1.

Pyridinium Chlorochromate: Specimens tested for pyridinium chlorochromate and found to be positive were also evaluated by gas chromatography/mass spectrometry to confirm the presence of the adulterant.

Sodium hypochlorite (bleach): Specimen were tested for bleach and found to be positive were also evaluated using an AquaCheck dipstick to confirm the presence of chlorine.

Carryover—High concentrations of nitrite, pyridinium chlorochromate and bleach were evaluated along with negative controls to determine the level at which carryover occurs in the testing process.

Olympus AU 5061 and AU800 chemistry analyzers were used for recording absorbance spectra.

In each of these assays the target adulterant was spiked into deionized water for nitrite and urine for pyridinium chlorochromate and bleach and then DPD/creatinine reagent prepared as per Example 1 was added as described below.

2(a) Na Nitrite Evaluation with DPD/creatinine Reagent

Table 3 sets out results observed when solutions containing increasing concentrations of sodium nitrite were treated with the DPD/creatinine reagent described in Example 1. Water was spiked with sodium nitrite to give different concentrations of nitrite as the starting point for generating an absorbance curve. Urine could not be used as nitrites often occur naturally in some urine samples. Spiked samples were processed through an Olympus AU800 autoanalyzer which sampled a 3 μl aliquot of the spiked specimen, mixed it with 250 ml of the DPD/creatinine reagent described in Example 1 and 250 ml of deionized water. The analyzer control software was set to S1=0 and E1=2 and a reading was taken at 410 nm.

Readings up to 200 μg/ml are considered to be reflect unadulterated samples. Samples with readings between 201 and 499 μg/ml are flagged as being unacceptable and samples with readings of 500 μg/ml or higher are retested for nitrites using a second colorometric assay.

TABLE 3

| Nitrite Conc - μg/ml | Nitrite Evaluation with DPD/Creatinine Reagent Assayed Values (concentration units) | | | | | Average |
|---|---|---|---|---|---|---|
| 50 | 54 | 56 | 56 | 55 | 50 | 54 |
| 100 | 106 | 112 | 108 | 108 | 106 | 108 |
| 250 | 246 | 267 | 260 | 263 | 256 | 258 |
| 375 | 373 | 398 | 383 | 379 | 372 | 381 |
| 500 | 479 | 504 | 501 | 491 | 487 | 492 |
| 625 | 597 | 645 | 619 | 629 | 611 | 620 |
| 750 | 690 | 737 | 729 | 733 | 700 | 718 |
| 1000 | 885 | 961 | 930 | 905 | 905 | 917 |
| 2000 | 1498 | 1553 | 1561 | 1580 | 1475 | 1533 |
| 3000 | 1887 | 1997 | 1928 | 1931 | 1881 | 1925 |
| | Series 1 | Series 2 | Series 3 | Series 4 | Series 5 | Series 6 |

2(b) Pyridinium Chlorochromate Evaluation with DPD/creatinine Reagent

Figure 4:
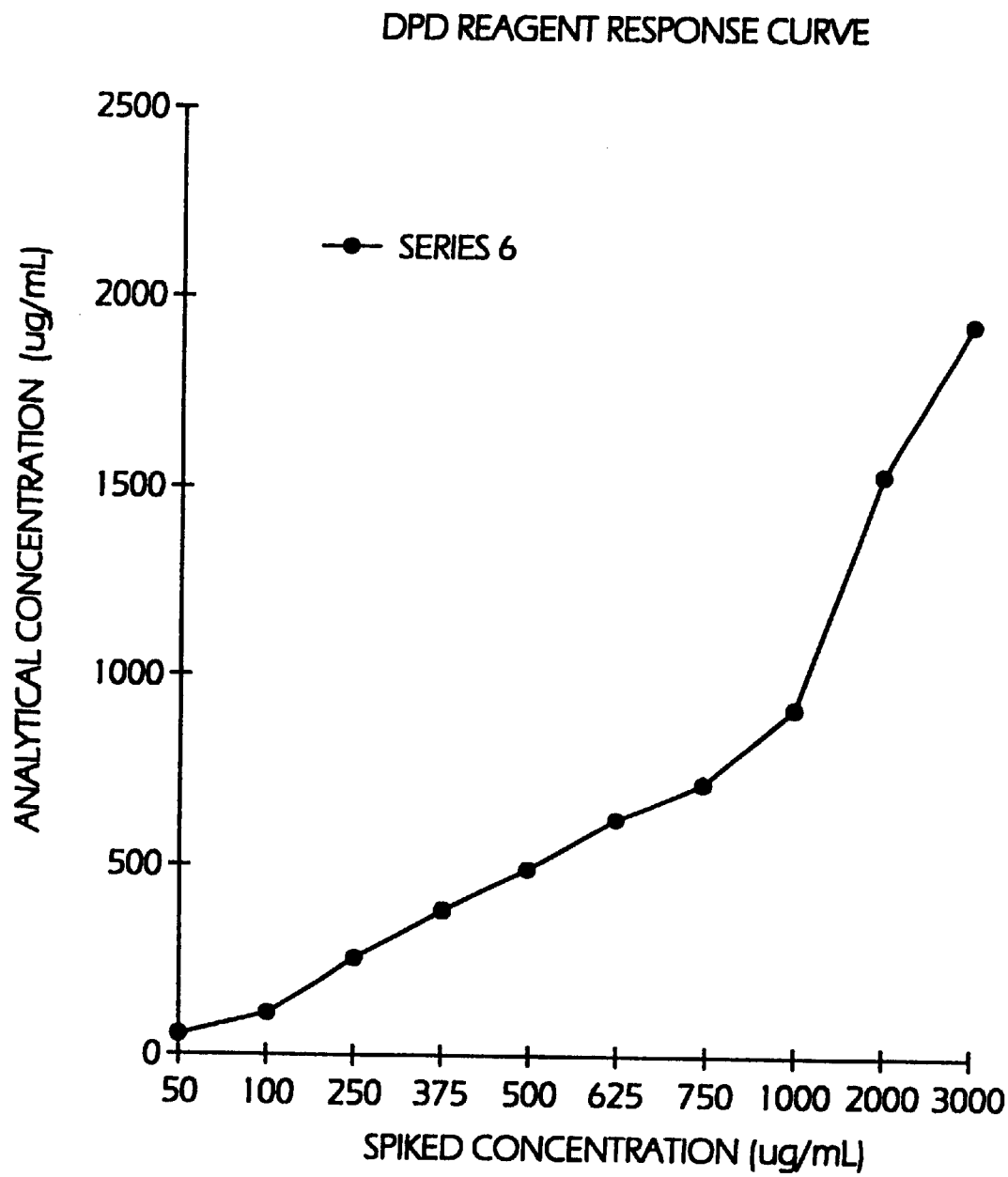
FIG. 4 is a graphical representation of measured concentration vs spiked concentration data from an evaluation study involving solutions of sodium nitrite treated with DPD and creatinine.

Urine was spiked with various amounts of pyridinium chlorochromate as the starting point for generating an absorbance curve. Spiked samples were processed through an Olympus AU800 autoanalyzer which sampled a 3 μl aliquot of the spiked specimen, mixed it with 250 ml of the DPD/creatinine reagent described in Example 1 and 250 ml of deionized water. The analyzer control software was set to S1=0 and E1=2 and a reading was taken at 540 nm. Table 4 contains the data from five runs and FIG. 4 is a graph of these results.

Based on the instrument printouts in concentration node, readings greater than −100 μg/ml are considered to be reflect unadulterated samples and readings of less than or equal to −100 μg/ml are subjected to alternative testing to confirm the presence or absence of pyridinium chlorochromate.

TABLE 4

| Conc μg/ml | Evaluation of Pyridinium Chlorochromate with DPD/creatinine Reagent Assayed Values (concentration units) | | | | | Average |
|---|---|---|---|---|---|---|
| 50 | −40 | −41 | −42 | −36 | −42 | −40 |
| 75 | −60 | −61 | −63 | −62 | −63 | −62 |
| 112.5 | −85 | −89 | −92 | −86 | −87 | −88 |
| 125 | | −101 | −104 | −99 | −103 | −102 |
| 150 | −116 | −123 | −123 | −118 | −121 | −120 |
| 187.5 | −147 | −153 | −154 | −154 | −154 | −152 |
| 225 | −176 | −186 | | −175 | −172 | −177 |
| 500 | −372 | −403 | −403 | −407 | −390 | −395 |
| 1000 | −757 | −802 | −786 | −779 | −750 | −775 |
| 2000 | −1399 | −1472 | −1460 | −1410 | −1416 | −1431 |
| 3000 | −2017 | −2092 | −2110 | −2068 | −2045 | −2066 |
| 4000 | −2596 | −2724 | −2687 | −2665 | −2644 | −2663 |
| | Series 1 | Series 2 | Series 3 | Series 4 | Series 5 | Series 6 |

2(c) Evaluation of DPD/creatinine as a test for Na hypochlorite

Figure 5:
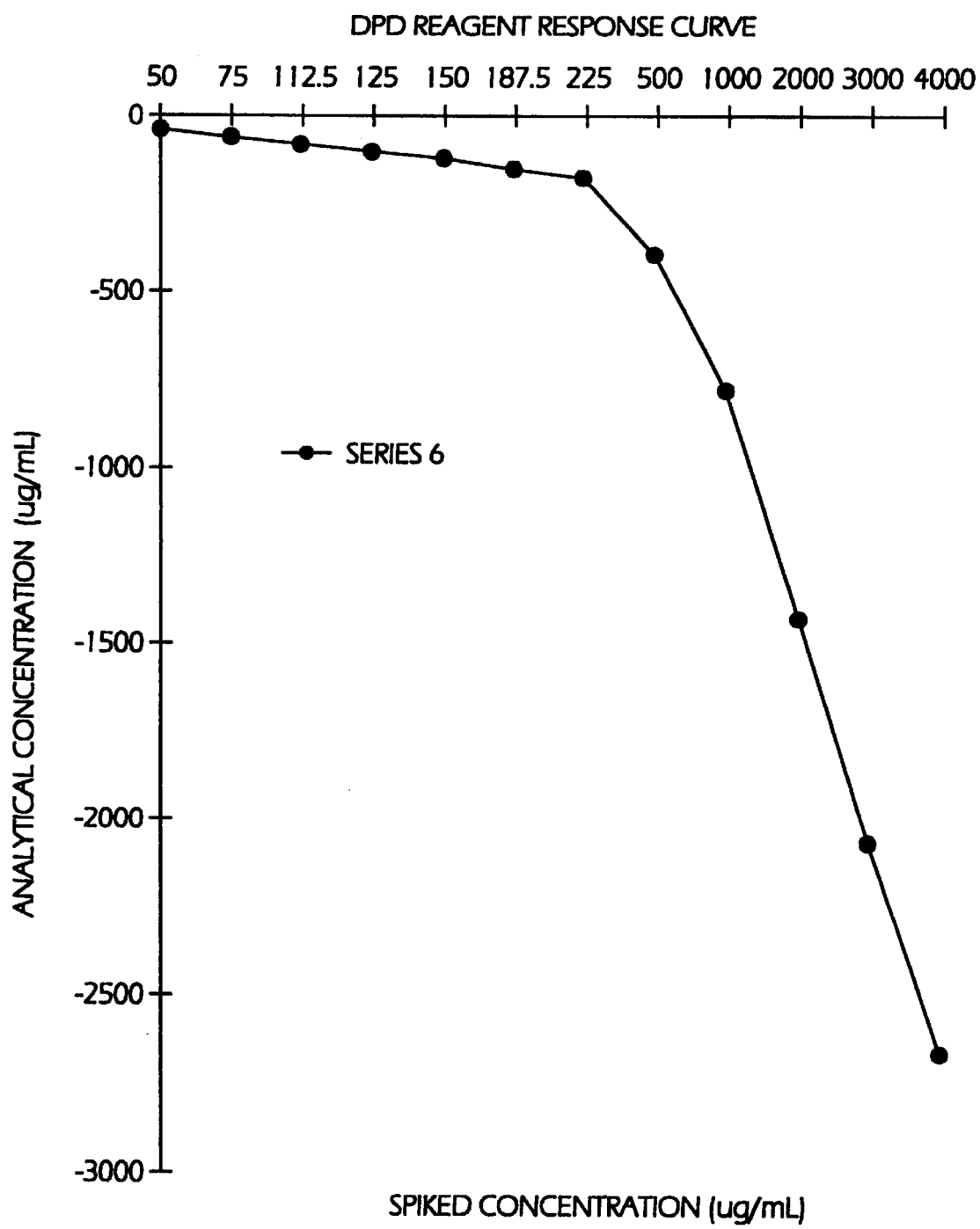
FIG. 5 is a graphical representation of measured concentration vs spiked concentration data from an evaluation study involving solutions of pyridinium chlorochromate treated with DPD and creatinine.
Figure 6:
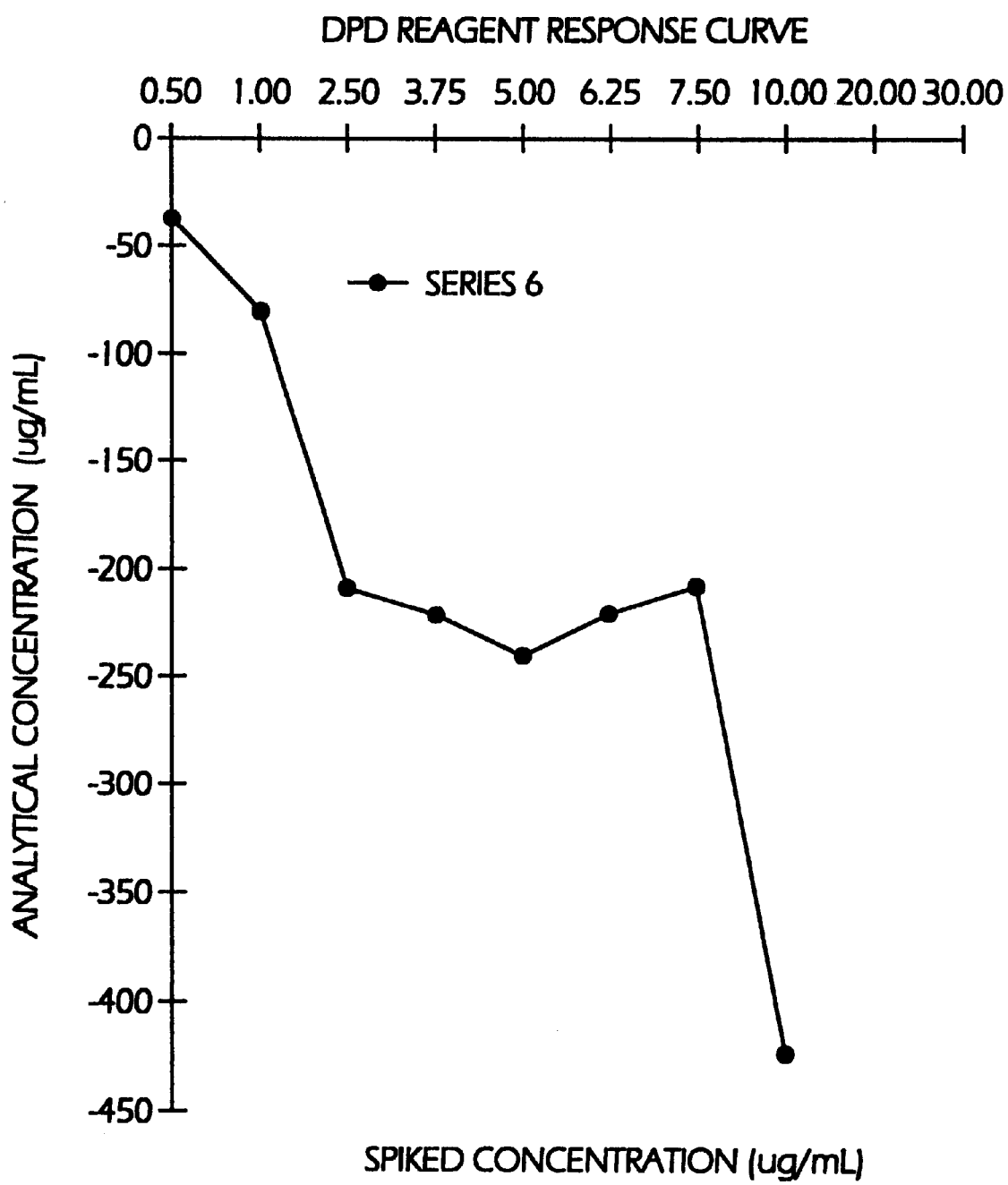
FIG. 6 is a graphical representation of measured concentration vs spiked concentration data from an evaluation study involving solutions of sodium hypochlorite treated with DPD and creatinine.

Urine was spiked with various amounts of sodium hypochlorite as the starting point for generating an absorbance curve. Spiked samples were processed through an Olympus AU800 autoanalyzer which sampled a 3 μl aliquot of the spiked specimen, mixed it with 250 ml of the DPD/creatinine reagent described in Example 1 and 250 ml of deionized water. The analyzer control software was set to S1=0 and E1=2 and a reading was taken at 540 nm. Results are given in Table 5 and in graphic form in FIG. 5.

Based on the instrument printout in concentration mode, readings of greater than −100 μg/ml are considered to represent normal unadulterated samples and readings equal to or less than −100 μg/ml or higher are confirmed by a second test for chlorine.

TABLE 5

| Conc* | Evaluation of Sodium Hypochlorite with DPD Reagent Assayed Values (Absorbance units) | | | | | Average |
|---|---|---|---|---|---|---|
| 0.50 | −61 | −9 | −36 | −42 | −9 | −37 |
| 1.00 | −101 | −25 | −71 | −124 | −29 | −80 |
| 2.50 | −256 | −158 | −231 | −183 | −03 | −184 |
| 3.75 | −122 | | −303 | −234 | −147 | −202 |
| 5.00 | −304 | −151 | −289 | −211 | 135 | −218 |
| 6.25 | −267 | −143 | −275 | −191 | −131 | −201 |
| 7.50 | −256 | −130 | −268 | −173 | −113 | −188 |
| 10.00 | −278 | −269 | −747 | −390 | −349 | −407 |
| 20.00 | −1734 | Abs Error | Abs Error | Abs Error | Abs error | |
| 30.00 | Abs Error | Abs Error | Abs Error | Abs Error | Abs error | |
| | Series 1 | Series 2 | Series 3 | Series 4 | Series 5 | Series 6 |

*Percent volume/volume of a Na hypochlorite solution containing 5.25% sodium hypochlorite

What is claimed is:

1. A colorometric method for detecting an oxidizing adulterant in urine, the method comprises:
    (a) mixing a reagent with a urine sample, the reagent comprising N,N-diethyl-1,4-phenlene diamine and creatine, and
    (b) detecting an absorption peak associated with the presence of the oxidizing adulterant.

2. A method according to claim 1 wherein oxidizing adulterant is nitrite.

3. A method according to claim 1 wherein oxidizing adulterant is a pyridinium chlorochromate.

4. A method according to claim 1 wherein the oxidizing adulterant is a hypochlorite.

5. A method according to claim 1 wherein the reagent comprises about 0.8 g/L of N,N-diethyl-1,4-phenylene diamine.

6. A method according to claim 1 wherein the reagent comprises about 0.4 g/L of N,N-diethyl-1,4-phenylene diamine at time of absorption reading.

7. A method according to claim 1 wherein the reagent comprises about 3.8 g/L of creatinine.

8. A method according to claim 1 wherein the reagent comprises about 1.9 g/L of creatinine at time of absorption reading.

9. A colorometric method for detecting an oxidizing adulterant in urine, the method comprises:

(a) mixing a reagent with a urine sample, the reagent comprising about 0.8 g/L of N,N-diethyl-1,4-phenylene diamine and about 3.8 g/L of creatinine, and (b) detecting an absorption peak associated with the presence of the oxidizing adulterant.

10. A colorometric method for detecting an oxidizing adulterant in urine, in in urine, the method comprises:

(a) mixing a reagent with a urine sample, the reagent comprising N,N-diethyl-1,4-phenylene diamine and creatinine and (b) detecting at least two absorption peaks associated with the presence of the oxidizing adulterant.

* * * * *

UNITED STATES PATENT AND TRADEMARK OFFICE
CERTIFICATE OF CORRECTION

PATENT NO.    : 6,303,384 B1
DATED         : October 16, 2001
INVENTOR(S)   : Mills et al.

It is certified that error appears in the above-identified patent and that said Letters Patent is hereby corrected as shown below:

<u>Column 8,</u>
Line 58, after "comprising N,N-diethyl-1," change "4phenlene" to -- 4phenylene --.

<u>Column 10,</u>
Line 7, after "adulterant in urine," delete "in in urine".

Signed and Sealed this

Twenty-third Day of September, 2003

JAMES E. ROGAN
*Director of the United States Patent and Trademark Office*